US006974595B1

(12) United States Patent
Reiner et al.

(10) Patent No.: US 6,974,595 B1
(45) Date of Patent: Dec. 13, 2005

(54) PHARMACEUTICAL COMPOSITIONS BASED ON DICLOFENAE

(75) Inventors: Alberto Reiner, Como (IT); Giorgio Reiner, Como (IT)

(73) Assignee: ProEthic Pharmaceuticals, Inc., Montgomery, AL (US)

( * ) Notice: Subject to any disclaimer, the term of this patent is extended or adjusted under 35 U.S.C. 154(b) by 0 days.

(21) Appl. No.: 09/524,747

(22) Filed: Mar. 14, 2000

Related U.S. Application Data

(63) Continuation-in-part of application No. 09/192,493, filed on Nov. 17, 1998, now abandoned, which is a continuation of application No. PCT/EP97/02709, filed on May 15, 1997.

(30) Foreign Application Priority Data

May 17, 1996 (IT) ............................... MI96A0992

(51) Int. Cl.$^7$ ........................ A61K 33/00; A61K 45/06
(52) U.S. Cl. .................... 424/722; 424/717; 562/454; 562/456; 562/457; 560/47; 514/553; 514/557; 514/576
(58) Field of Search ............................... 424/722, 717; 562/454, 456, 457; 560/47; 514/553, 557, 514/576

(56) References Cited

FOREIGN PATENT DOCUMENTS

| EP | 0 466 650 A2 | 1/1992 | | |
|---|---|---|---|---|
| EP | 466650 | * | 1/1992 | ........... A61K 33/00 |

OTHER PUBLICATIONS

Henry, D., et al; "Variability in risk of gastrointestinal complications with individual non-steroidal anti-inflammatory drugs: results of a collaborative meta-analysis"; BMJ; vol. 312, pp. 1563-1566, (1996).
Walker, A.M.; "Quantitative studies of the risk of serious heptatic injury in persons using nonsteroidal antiinflammatory drugs"; Arthritis and Rheumatism, vol. 40, No. 2, pp. 201-208 (1997).
Gutthann, S.P., et al; "Nonsteroidal anti-inflammatory drugs and the risk of hospitalization for acute renal failure"; Arch. Intern. Med., vol. 156, pp. 2433-2439, (1996).
Amidon, G.L., et al; "A theoretical basis for a biopharmaceutic drug classification: The correlation of in vitro drug product dissolution and in vivo bioavailability"; Pharm. Research, vol. 12, No. 3, pp. 413-420, (1995).
Neuvonen, P.J., "The effect of magnesium hydroxide on the oral absorption of ibuprofen, ketoprofen and diclofenac"; Br. J. Clin. Pharmac. vol. 31, pp. 263-266, (1991).
Neuvonen, P.J., et al; "Enhancement of drug absorption by antacids"; Clin. Pharmacokinet. 27 (2): pp. 120-128, (1994).
Neuvonen, P.J., et al; "Effect of magnesium hydroxide on the absorption of tolfenamic and mefenamic acids"; Eur. J. Clin. Pharmacol, 35: pp. 495-501, (1988).
Derendorf, H., et al; "Pharmacokinetics of diclofenac sodium after intramuscular administration in combination with triamcinolone acetate"; Eur. J. Clin. Pharmacol., 31: 363-365 (1986).
Terhaag, B., et al; "Bioavailability of a new effervescent tablet of diclofenac"; Int. J. Clin. Pharmacol. Ther., 38:546: 551 (2000).
Lotsch, J., et al.; "Population pharmacokinetics of fast release oral diclofenac in healthy volunteers: relation to pharmacodynamics in an experimental pain model"; Pharmaceutical Research, vol. 17, No. 1, pp. 77-84, (2000).
Marzo, A., et al; "Pharmacokinetics of Diclofenac after oral administration of its potassium salt in sachet an tabled formulations"; Arzneim. Forsch., 50:43-47 (2000).
Reiner, V., et al; "Increased absorption rate of diclofenac from fast acting formulations containing its potassium salt"; Arzneim. Forsch., 51:885-890 (2001).
Brogden, R.N., et al; "Diclofenac sodium: A review of its pharmacological properties and therapeutic use in rheumatic diseases and pain of varying orgin"; Drugs, 20: pp. 24-48, (1980).
Macia, M.A., et al; "Comparative bioavailability of a dispersible formulation of diclofenac and finding of double plasma peaks"; Int. J. Clin Pharmacol. Ther., 33:333-339 (1995).
Bettmi, R., et al; "Swelling force development as a result of hydrate formation in diclofenac sodium or nitrofurantoin tablets"; S.T.P. Pharma Sciences 10 (4) pp. 335-339, (2000).
Henrikson, P.A., et al; Absorption and effect of diclofenac sodium after surgical removal of a ower wisdom tooth; Curr. Ther. Res., 31:30-26 (1982).
Degen, P.H., et al; "Pharmacokinetics of diclofenac and five metabolites after single doses in healthy volunteers and after repeated doses in patients"; Xenobiotica, 18:1449-1455 (1988).
Maggi, C.A., et al; "Comparative bioavailability of diclofenac hydroxyethylpyrrolidine vs diclofenac sodium in man"; Eur. J. Clin. Pharmacol., 38:207-208 (1990).

(Continued)

*Primary Examiner*—James O. Wilson
*Assistant Examiner*—Howard V. Owens, Jr.
(74) *Attorney, Agent, or Firm*—Clark G. Sullivan; King & Spalding

(57) ABSTRACT

New pharmaceutical compositions for oral use containing Diclofenac together with alkali metal bicarbonates in amounts of from 20 to 80 by weight with respect to Diclofenac are described. These compositions are entirely palatable and free from any unpleasant taste or other side effects; in particular, these formulations permit to obtain in human patients higher $C_{max}$ of the active principle and shorter $T_{max}$ together with a lower coefficient of variation.

43 Claims, 10 Drawing Sheets

OTHER PUBLICATIONS

Figure 1:
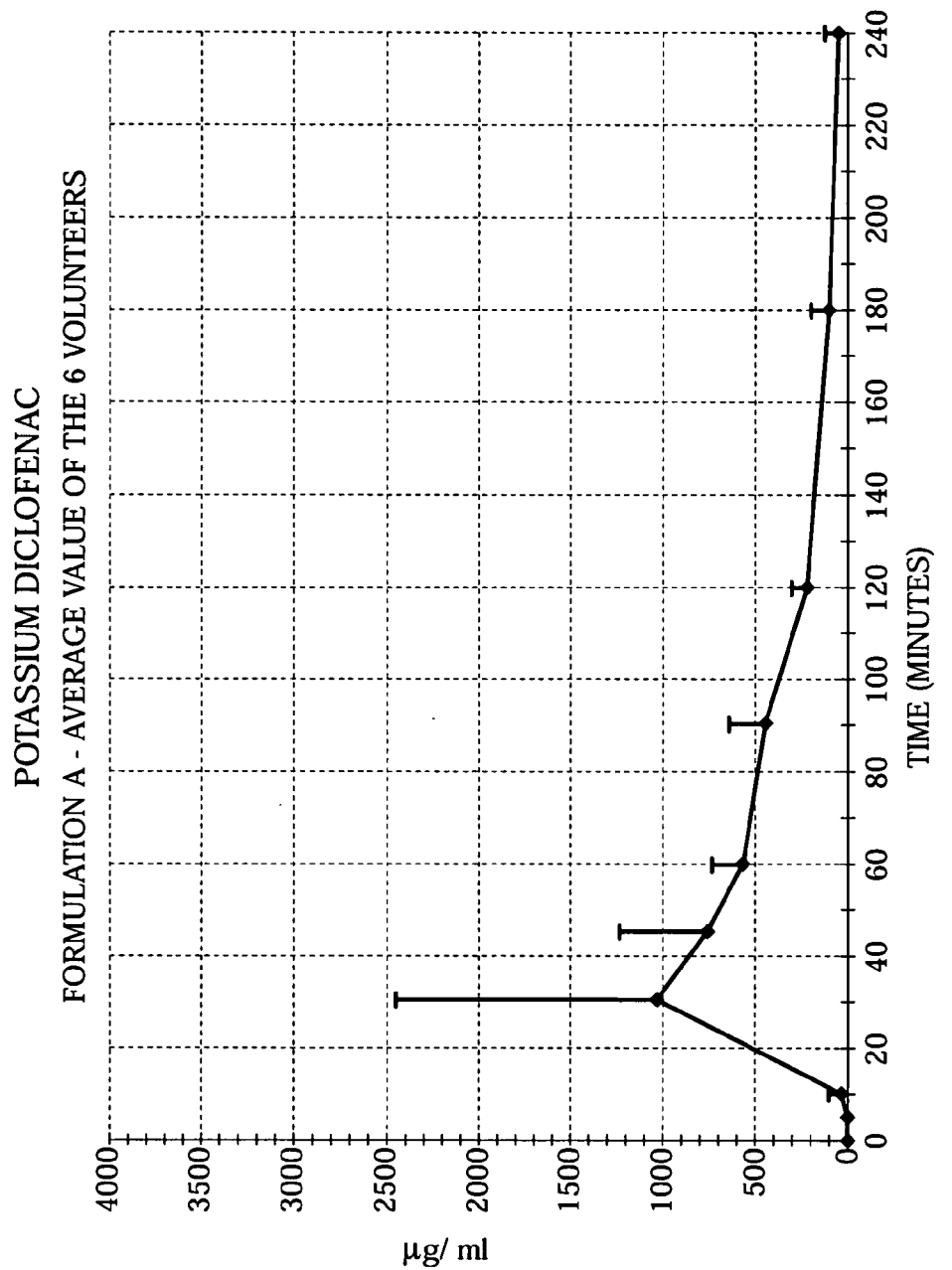

Mendes, G.B.B., et al; "Comparative bioavailability of two suspension formulations of potassium diclofenac in healthy male volunteers"; Int. J. Clin. Pharmacol. Thr., 32:131-135 (1994).

Crook, P.R., et al; "The pharmacokinetics of diclofenac sodium in patients with active rheumatoid disease"; Eur. J. Clin. Pharmacol., 21:331-334 (1982).

Willis, J.V., et al; "The pharmacokinetics of diclofenac sodium following intravenous and oral administration"; Eur. J. Clin. Pharmacol., 16:405-410 (1979).

Willis, J.V., et al; "The influence of food on the absorption of diclofenac after single and multiple oral doses"; Eur. J. Clin. Pharmacol., 19:33-37 (1981).

Riess, W., et al; "Pharmacokinetics and metabolism of the anti-inflammatory agent Voltaen" Scand. J. Reumatol., Suppl. 22:17-29 (1978).

Physicians' Desk Reference; Novartis Pharmaceutical Corp., pp. 1830-1832 (2000).

* cited by examiner

PHARMACEUTICAL COMPOSITIONS BASED ON DICLOFENAE

This application is a continuation-in-part of application Ser. No. 09/192,493, filed Nov. 17, 1998, now abandoned, which is a continuation of PCT/EP97/02709, filed May 15, 1997.

The present invention relates to new immediate release pharmaceutical compositions containing [(2,6-dichloro-anilino)-2-phenyl]-2-acetic acid (more commonly known as Diclofenac) in acid and/or salt form.

Diclofenac is a non-steroidal drug which was invented at the end of the sixties by A. Sallmann and R. Pfister (NL-6, 604,752 and U.S. Pat. No. 3,558,690 both to Ciba-Geigy) and whose structural formula is indicated below.

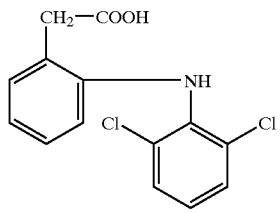

Diclofenac is widely dispensed and used owing to its well-known analgesic, anti-pyretic, anti-arthritic, anti-phlogistic and anti-rheumatic properties and it is generally taken orally in the form of normal tablets or tablets covered with coatings resistant to gastric juices, or rectally, or by injection, or topically. The possibility of taking it in the form of sweets, tablets dissolving in the mouth, drages, chewing gum or other similar pharmaceutical forms or in formulations for the extemporary preparation of Diclofenac-based aqueous solutions and/or suspensions would represent a different mode of administration which is definitely more suitable, especially for children and elderly persons.

Owing to its poor solubility in water, Diclofenac is normally used in salt form; the salts of Diclofenac customarily used are those of sodium, potassium or other alkali and alkaline earth metals, together with salts of organic nature, such as the salts of basic amino acids, such as lysine, arginine and ornithine, or other pharmacologically acceptable organic bases which have the ability to render the resulting salt soluble in water.

The pharmaceutical compositions of the Diclofenac salts for oral use are generally accompanied by side effects of not inconsiderable consequence: Diclofenac salts are in fact characterised by a particularly unpleasant and bitter taste and by the fact that they produce a sensation of strong astringency and cause an especially intense form of irritation in the buccal cavity, especially in the area of the larynx. Although the first problem has been party solved by using flavourings which are able in some manner to mask the taste, satisfactory solutions have still not been proposed for the two remaining problems.

Therefore, the pharmaceutical compositions containing Diclofenac salts still have a poor palatability which limits their adoption and possible fields of application, despite the excellent therapeutic effect with which they are associated.

A second problem connected to Diclofenac is that, when it is orally administered by means of immediate release formulations, the corresponding $T_{max}$ (the time to the maximum plasma concentration) is usually located at about 1 hour since administration, this being of course a not completely satisfactory result when a prompt and strong analgesic/anti-pyretic effect is sought for. Furthermore, the corresponding coefficient of variation is normally in the range of 70–90%, which means that the $T_{max}$ is strongly variable and dependent on the physical characteristics of the patient (Physicians' Desk Reference, 52 edition, 1998, pag. 1831). Attempts are therefore still being made in order to enhance the rate of absorption of Diclofenac and to provide an earlier onset of the therapeutical effect (N. Davies, K. Anderson; Clinical Pharmacokinetic of Diclofenac, Clin.Pharmacokinet., 1997, Sep. 33(3).

The object of the present invention is therefore that of providing a fully palatable formulation of Diclofenac which is able to generate a more rapid, uniform and foreseeable release of the active principle if compared to the compositions known in the art and presently available on the market. For the purposes of the present invention $T_{max}$ means the time to the maximum plasma concentration whereas $C_{max}$ is the maximum plasma concentration of the active principle, namely Diclofenac. It has now been found that, by adding alkali metal bicarbonates or mixtures thereof to the Diclofenac in its acid and/or salt form, in amounts of from 20 to 80 % by weight based on the acid-form of Diclofenac, pharmaceutical compositions can be obtained which are substantially free from the side effects mentioned above. The first object of the present invention is therefore represented by a pharmaceutical formulation for oral use containing Diclofenac ill acid and/or Salt form together with alkali metal bicarbonates or mixtures thereof and customary excipients and adjuvants, wherein said alkali metal bicarbonates are present in amounts of from 20 to 80% by weight based on the weight of Diclofenac. It has in fact been surprisingly demonstrated that the use of alkali metal bicarbonates in the above-mentioned ratio permits to achieve constant, reproducible and foreseeable blood levels of the active ingredient, with the consequent indisputable advantages from the therapeutic point of view; furthermore, it has also been found that the combined use of Diclofenac together with alkali metal bicarbonates yields Diclofenac-based pharmaceutical compositions in which the active ingredient is released more rapidly compared with normal formulations, bringing about higher blood levels and therefore a more immediate therapeutic effect; finally the so-obtained immediate release formulations are substantially palatable and free from aftertaste.

According to the preferred embodiment of the present invention, the amount of alkali metal bicarbonates to be added is comprised between 40 and 80% by weight, based on the weight of the acid-form Diclofenac, whereas the alkali metal bicarbonates are selected from sodium and/or potassium bicarbonates, Diclofenac being normally present in the form of its sodium and/or potassium salts.

It has also been found, and forms a second subject of the present invention, that the addition of flavouring substances selected from mint, aniseed, ammonium glycyrrhizinate and mixtures thereof to the compositions containing the Diclofenac salts and alkali metal bicarbonates produces a synergistic effect which completely eliminates all the above-mentioned palatability/astringency effects, providing pharmaceutical compositions which are entirely palatable (and/or drinkable in the case of those used for the preparation of solutions and/or suspensions) and free from aftertaste.

The flavouring substances may be used as such or supported on inert materials, for example maltodextrin, in order to obtain a better distribution of the granulates and to facilitate excellent dispersibility of the flavouring in solution. Preferably, they are absorbed on maltodextrin with a power of 1 to 2000 and 1 to 1000.

The amount of flavouring substances in its pure form is also preferably from ⅓ to 3 times the weight of the acid-form Diclofenac.

These flavouring substances are used in the implementation of the present invention without altering their organoleptic properties and without depriving them of their intrinsic qualities of flavourings which are liposoluble and generally oily in the pure state.

As it will be clear from the examples, the immediate release formulations for oral use of the present invention containing from 10 to 60 mg of Diclofenac in acid and/or salt form together with alkali metal bicarbonates or mixtures thereof in amounts of from 20 to 80% by weight based on the weight of Diclofenac permit to generate in human patients an average $C_{max}$ of Diclofenac comprised between 400 and 2500 ng/ml independently on the age, sex or weight of the patients themselves.

Secondly, the formulations according to the present invention permit to obtain in humans an average $T_{max}$ of Diclofenac after 5÷30 minutes since administration, generally 13÷27, independently on the amount of Diclofenac contained therein and also independently on the age, sex, weight of the patient.

Furthermore, the $T_{max}$ of the formulations of the present invention show a coefficient of variation which is about 44–86% lower than the presently marketed formulations; this is evidently an extremely important result from the clinical point of view as it is now possible to have a therapeutical effect of Diclofenac which is foreseable, reproducible and independent on the sex, weight and health conditions of the patient.

Thus, the presently claimed Diclofenac-based formulations permit to achieve a higher $C_{max}$ in a shorter $T_{max}$ and with a lower coefficient of variation if compared to the formulations available on the market, with therapeutical advantages which do not need to be commented.

According to the best mode for carrying out the present invention the pharmaceutical formulations will contain from 10 to 60 mg/dose of diclofenac in its potassium or sodium salt form together with 40 to 80% by weight of potassium or sodium bicarbonate based on the weight of Diclofenac in its acid form, together with the usual excipients and adjuvants; even more preferably they will packaged as:

a sachet or tablet formulation containing 50 mg of Diclofenac potassium salt and 22 mg of potassium bicarbonate or 50 mg of Diclofenac sodium salt and 19 mg of sodium bicarbonate;

a sachet or tablet formulation containing 12.5 mg of Diclofenac sodium salt and 5.5 mg of potassium bicarbonate or 25 mg of Diclofenac sodium salt and 11 mg potassium bicarbonate.

It will be by the way evident to any skilled in this art that the present formulations can also be used as immediate release layers of multilayered release pharmaceutical formulations containing Diclofenac as one of the active ingredients; said formulations are therefore a further object of the present invention.

The following Examples are given purely by way of non-limiting illustration.

Example 1 - Composition dissolving instantly in water

Active ingredients

| | |
|---|---|
| 1) Diclofenac potassium salt* | 50 mg |
| 2) Potassium bicarbonate: | 22 mg |
| 3) Mint flavouring on maltodextrin(1:2000)**: | 60 mg |
| 4) Aniseed flavouring on maltodextrin (1:1000)***: | 104 mg |

Excipients and adjuvants

| | |
|---|---|
| 5) Saccharin: | 4 mg |
| 6) Aspartame: | 10 mg |
| 7) Mannitol: | 50 mg |
| 8) Saccharose*** *q.s.: | 2 g |

*If it is desired to prepare compositions based on Diclofenac sodium salt, it is advantageous to use sodium bicarbonate in a quantity of approximately 38% by weight based on the weight of the Diclofenac sodium salt present. Sodium carbonate may also be added to the sodium bicarbonate, maintaining the following optimum proportions: 27% of sodium bicarbonate and 4–5% of sodium carbonate, always based on the amount by weight of Diclofenac sodium salt present.
**The title of the pure mint essence, as obtained according to the Dean-Stark method, is of 18% by weight; the related amount is therefore in this case of 10.8 mg.
***The title of the pure anise essence, as obtained according to the Dean-Stark method, is of 14.5% by weight, the related amount is therefore in this case of 16 mg.
****The presence of saccharose is not strictly necessary; in its absence, a composition having a very limited granulate content is obtained which is perfectly soluble in contact with water. In that case, nothing is changed from the point of view of tolerability in contact with the mucosa and from the point of view of the palatability of the drinkable solution.

Preparation

Components 1, 2, 5, 6 and 7 are mixed in a suitable mixer, and the mixture so obtained is wetted with 95% ethanol. Granulation is carried out with a 66 mm mesh and the granulate is preferably dried in a current of air.

Components 3, 4 and 8, which have already been granulated using a mesh of the same granulometry, are then added and the whole is mixed.

The mixture is then introduced into a metering machine filling packets or similar containers.

Example 2 - Tablet for dissolving in the mouth

Active ingredients

| | |
|---|---|
| 1) Diclofenac potassium salt*: | 50 mg |
| 2) Potassium bicarbonate: | 35 mg |
| 3) Mint flavouring on maltodextrin** (1:2000) + gum arabic (E 414): | 50 mg |
| 4) Aniseed flavouring (1:1000) on maltodextrin*** + silicon dioxide (E 551): | 120 mg |

Excipients and adjuvants

| | |
|---|---|
| 5) Saccharin: | 50 mg |
| 6) Aspartame: | 12 mg |
| 7) Mannitol: | 20 mg |
| 8) Saccharose****: | 300 mg |

*to**** see Example 1

Example 3 - Gum tablet

Active ingredients

| | |
|---|---|
| 1) Diclofenac potassium salt*: | 50 mg |
| 2) Potassium bicarbonate: | 35 mg |
| 3) Mint flavouring on maltodextrin**: | 30 mg |
| 4) Aniseed flavouring on maltodextrin***: | 80 mg |

Excipients and adjuvants

| | |
|---|---|
| 5) Mannitol: | 30 mg |

-continued

| | |
|---|---|
| 6) Menthol: | 0.01 mg |
| 7) Gum base: | 600 mg |
| 8) Sorbitol: | 700 mg |
| 9) Saccharin: | 3 mg |
| 10) Hydroxypropylmethylcellulose: | 33 mg |
| 11) Colouring agent: | 7 mg |

*to*** see Example 1

Example 4

Comparative Test

The packaged composition containing 50 mg of Diclofenac potassium of Example 1 (formulation C) was subjected to a pharmacokinetic test for comparison with a similar composition not containing alkali metal carbonates and bicarbonates (formulation B), and with a second composition in tablet form (formulation A) produced by Ciba-Geigy (Voltaren Rapid®), also in this case not containing alkali metal carbonates and bicarbonates, both formulations A and B containing 50 mg of Diclofenac potassium.

This comparative evaluation was carried out on the same 6 healthy volunteers in accordance with the experimental plan described hereinafter.

Experimental scheme: Single-dose study using three methods in randomised cross-over with a wash-out of three days.

Sampling times: 0 h (before administration), 5 min, 10 min, 30 min, 45 min, 1 h, 1.5 h, 2 h, 3 h, 4 h, 6 h, 8 h, after each administration.

Blood sample treatment: 8Ml in heparinised test tubes, centrifugation for 15 min at 1500 rev/min, subdivided into two fractions and subsequently frozen at −20° C.

Times: wash-out of two days between treatments.

Determination method: HPLC, with internal standard, sensitivity 10 ng/ml.

Analysis Method

Column: Nova Pak C18, 3.9×150 mm, 4 $\mu$m Waters S.p.A.—Vimodrone, Italy.

Eluant: NaH2PO4 0.01 M+0.1% TEA, pH 3.0 (H3P04)/acetonitrile, 60/40.

Flow: 1.2 ml/min

Detection: UV/275 nm

Temperature: 30° C.

Injection: 50 al

Analysis time: 16 min.

Sample Preparation 10 al of the internal standard methanolic solution, and flufenamic acid (corresponding to 1320 ng) are added to 1 ml of defrosted plasma in 10 ml glass test tubes. The tubes are agitated in a Vortex mixer for 1 minute. 0.5 ml of a 0.5N HCl/1N NaCl solution is added. The whole is agitated in a Vortex mixer for 1 minute. 6 ml of a 95/5 n-hexane/isopropanol solution are added.

The mixture is then agitated in the Vortex mixer for a further 15 minutes. Centrifugation is carried out at 3000 rev/min for 15 minutes and the organic phase is transferred to fresh 10 ml glass test tubes and evaporated to dryness in a centrifugal evaporator under vacuum at ambient temperature. The whole is taken up in 200 al of a 70/30 acetonitrile/water solution, and the precipitate is dissolved under ultrasound for 2 minutes.

Figure 2:
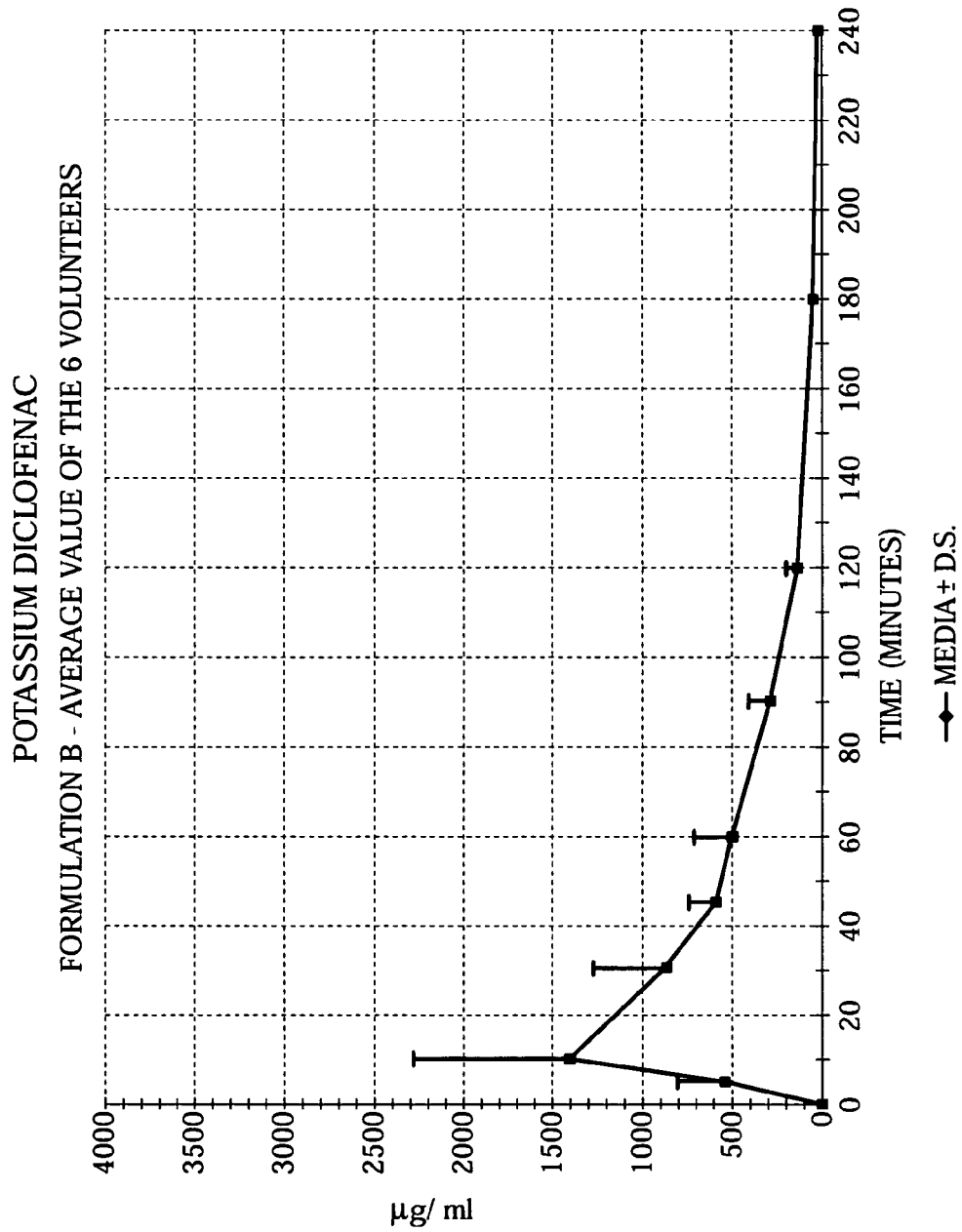
Figure 3:
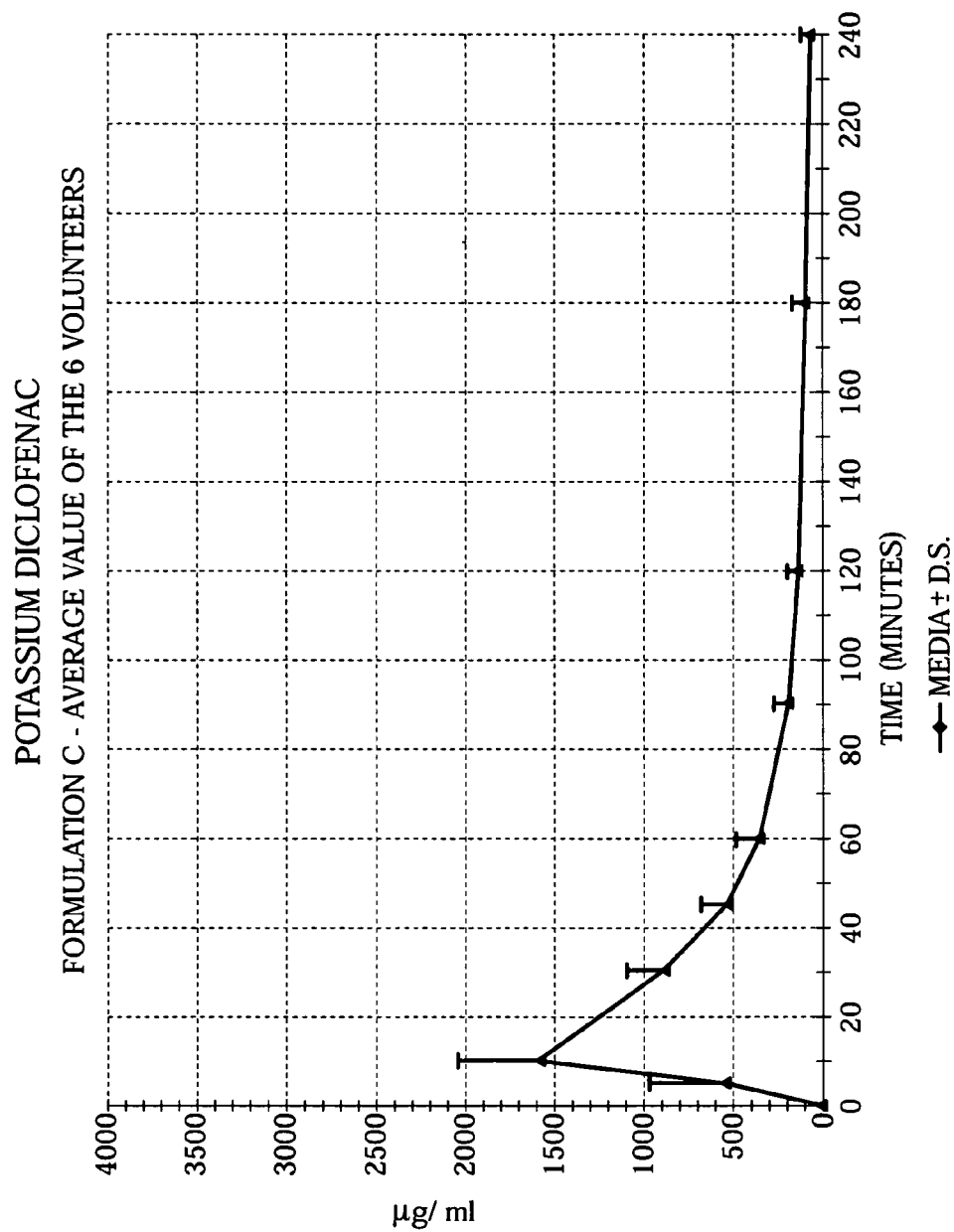
Figure 4:
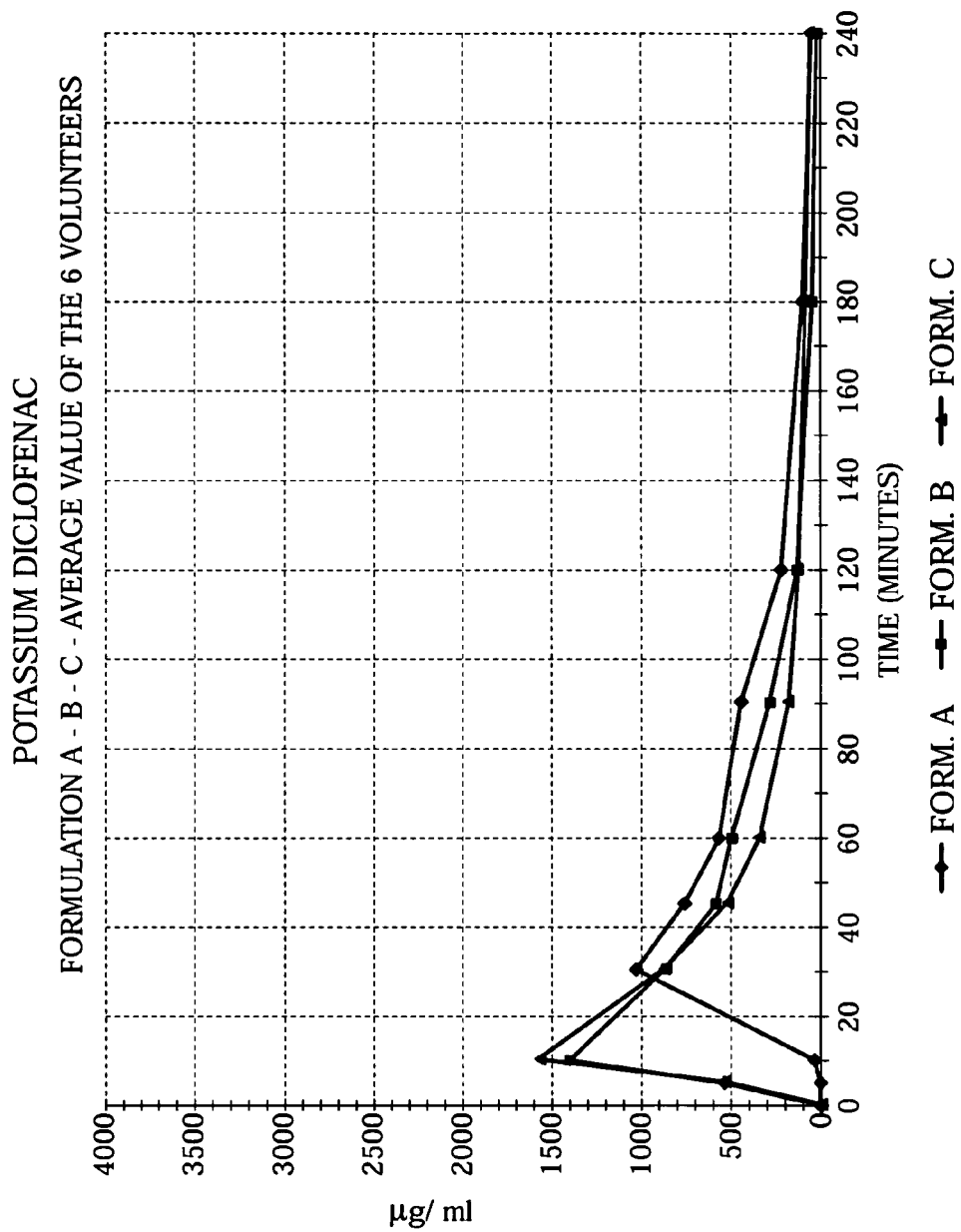
Figure 5:
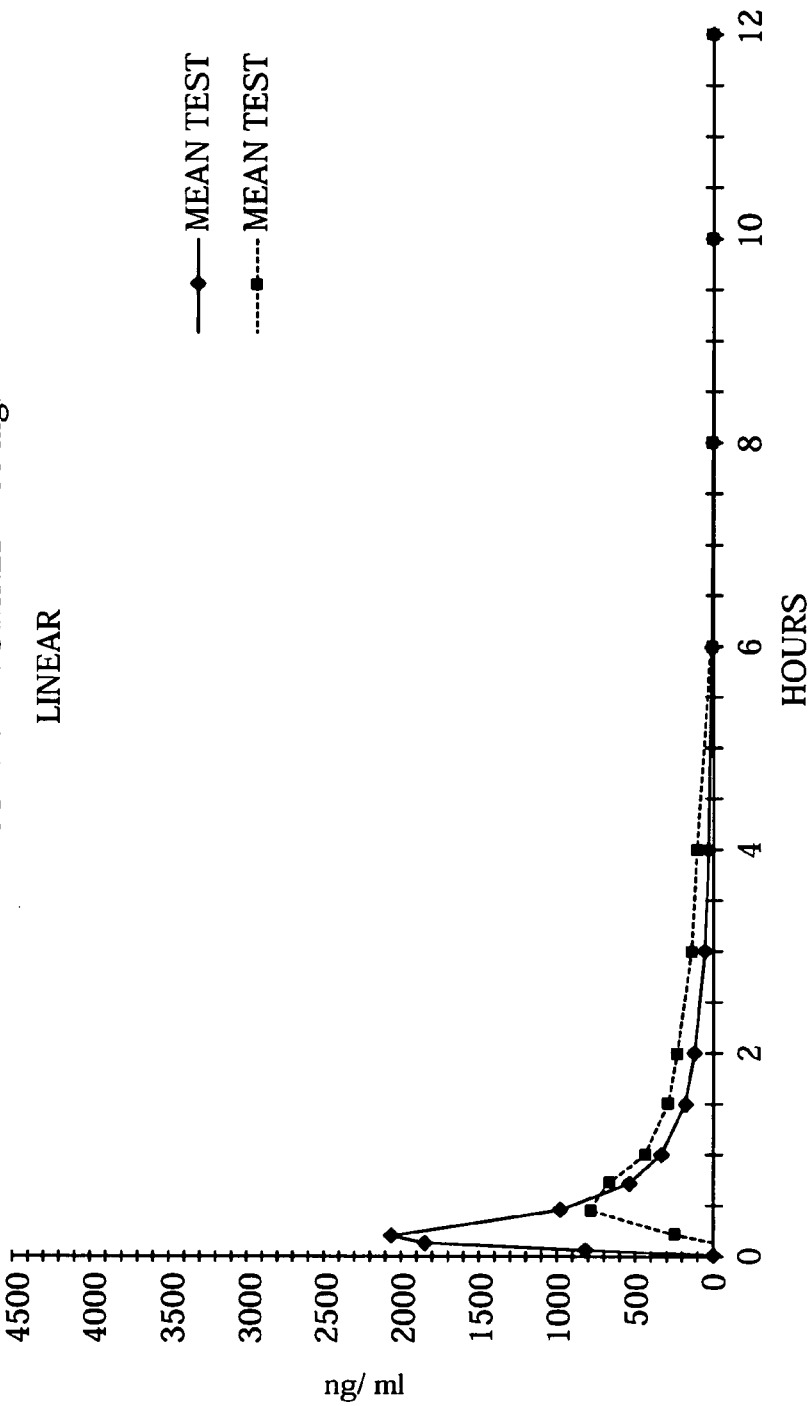
Figure 6:
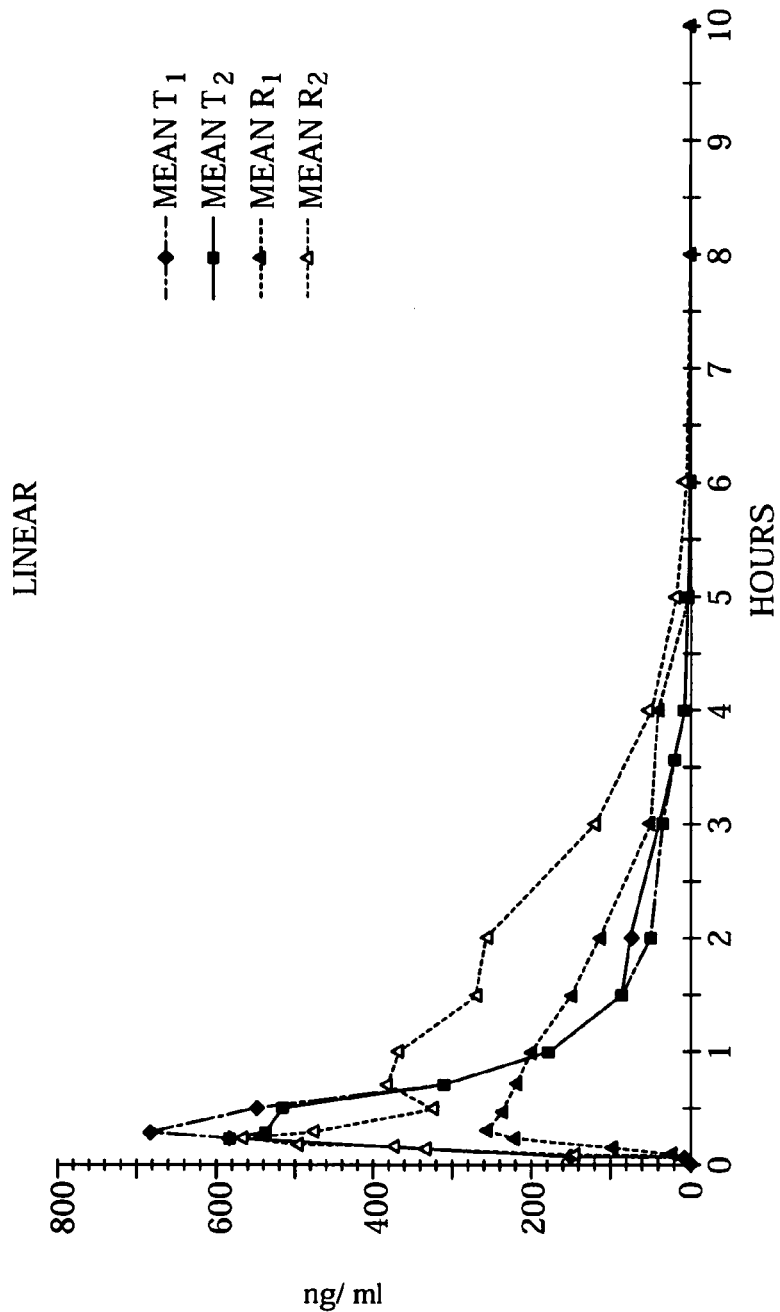

FIGS. 1, 2 and 3 show the concentrations of Diclofenac in the blood of the six volunteers as regards formulations A, B (Ciba-Geigy comparative formulations) and C (formulation corresponding to the composition of Example 1), respectively. As will be appreciated, the blood concentration of the formulation of the present invention has, compared with the comparative formulations, a more constant and uniform pattern. This characteristic is also found in FIGS. 4, 5 and 6 which show the average values corresponding to the blood levels of the six volunteers together with the corresponding standard deviation.

The result is clear and surprising: compared with the sample compositions, the compositions of the present invention permit constant, reproducible and foreseeable blood levels of the active ingredient, irrespective of the characteristics of the volunteer (weight, age, etc), with the consequent indisputable advantages from the therapeutic point of view.

Figure 7:
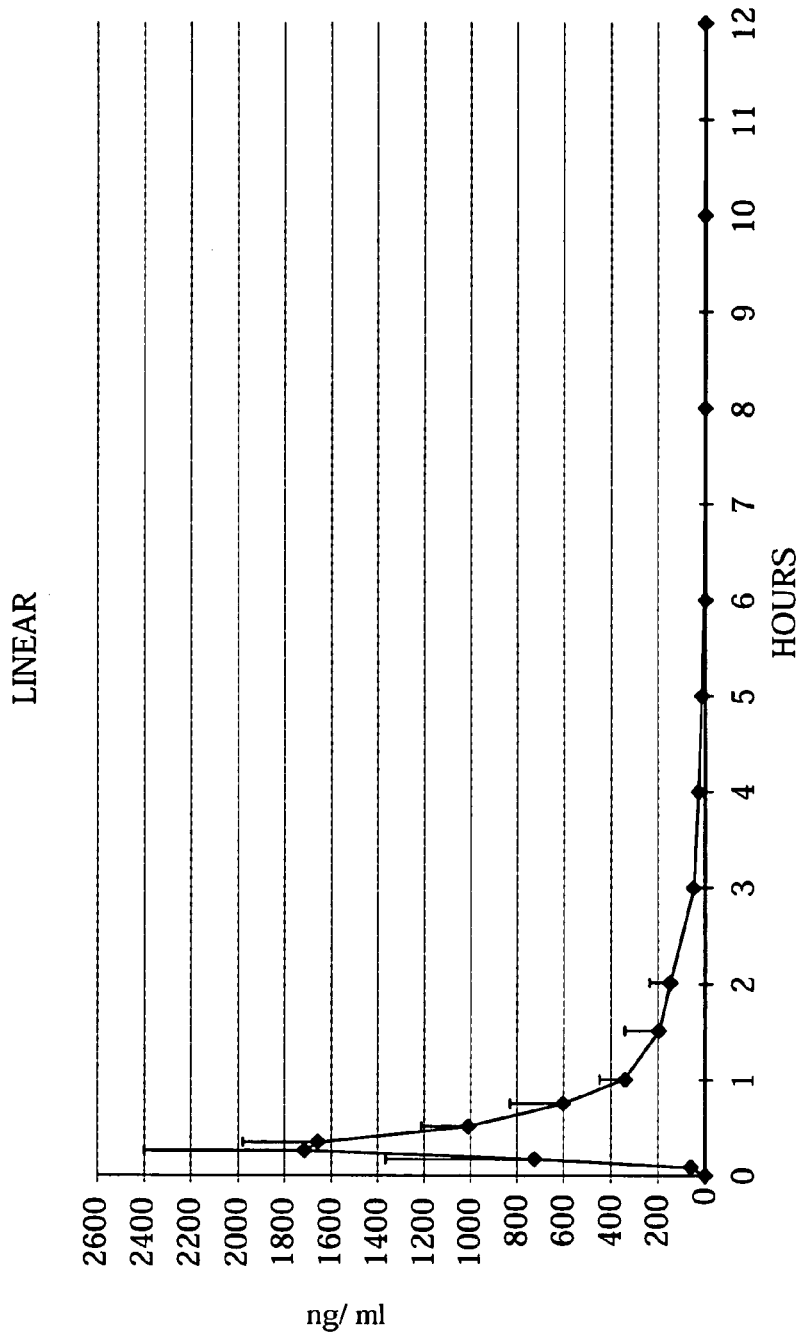
Figure 8:
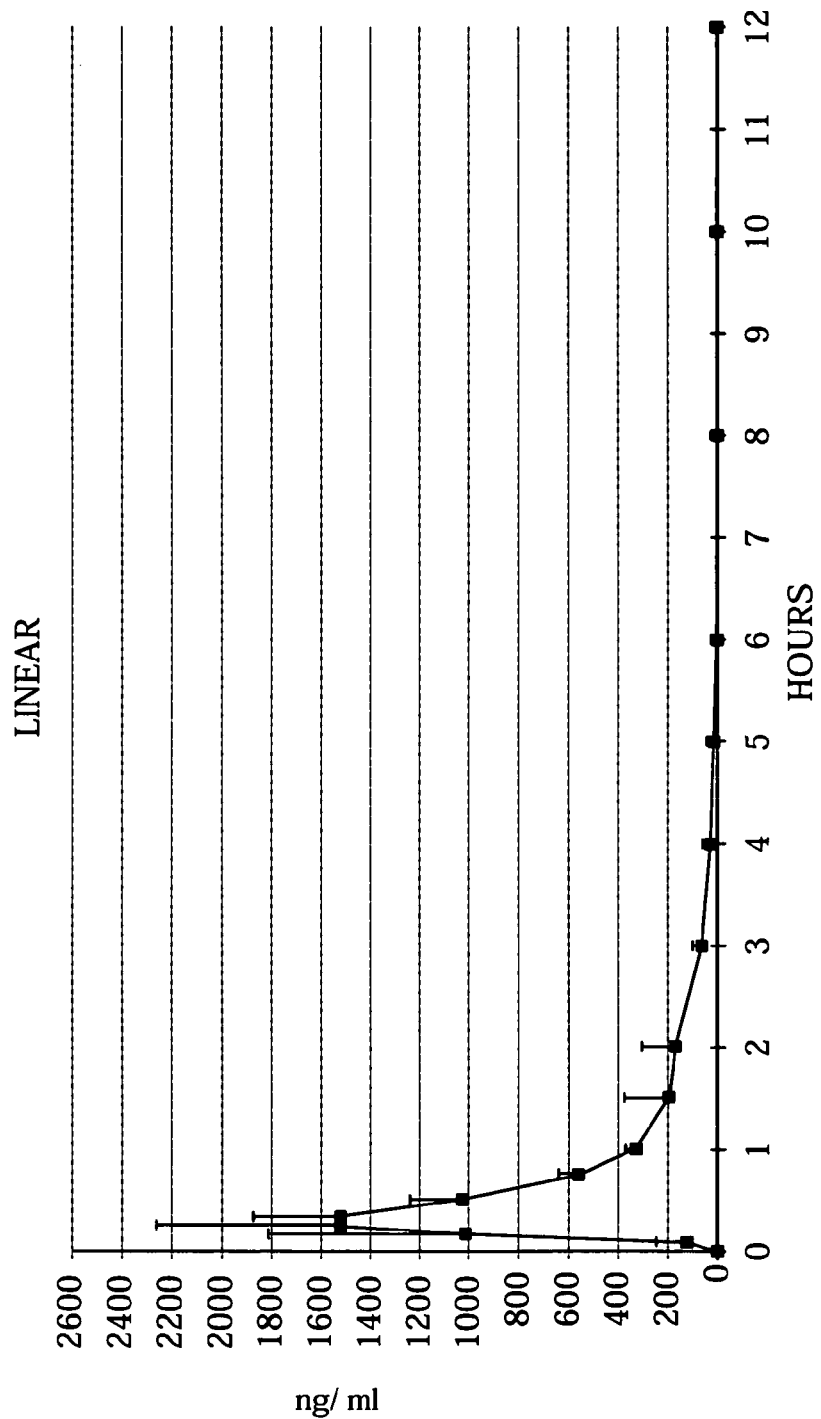
Figure 9:
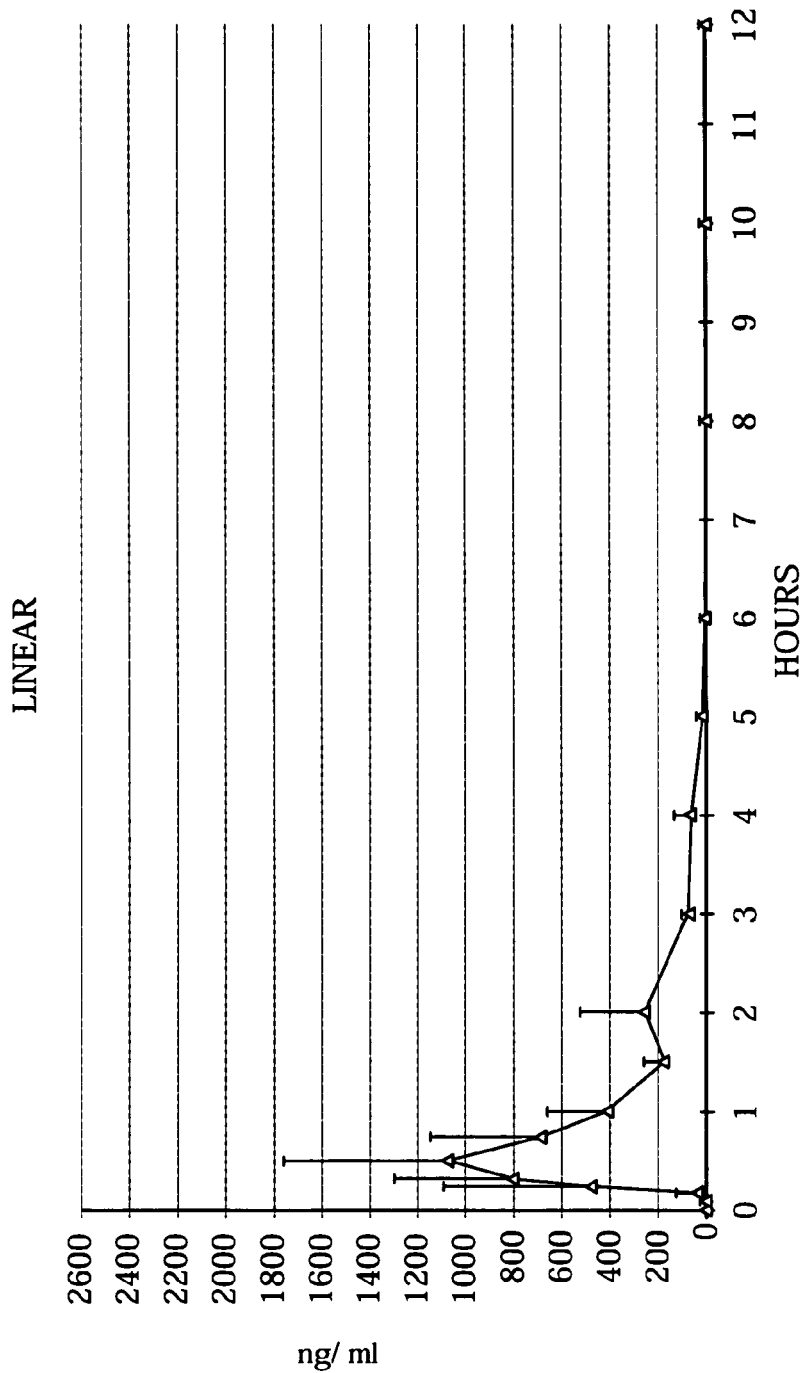
Figure 10:
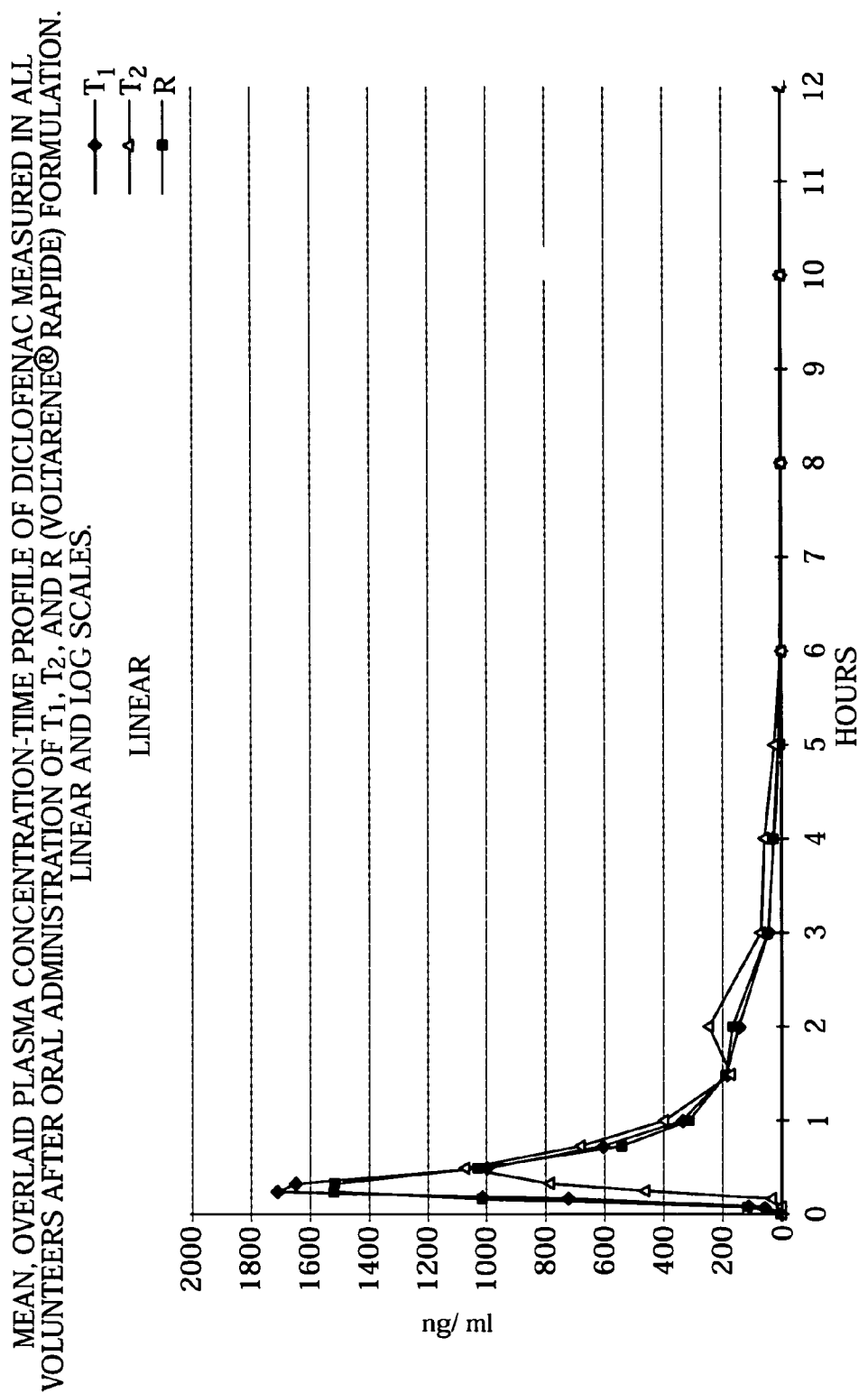

Finally, FIG. 7 shows, by comparison, the graphs relating to the average values of the six volunteers (that is to say, the preceding FIGS. 4, 5 and 6); as will be noted, the formulation of the present invention permits, in addition to the advantages already mentioned, the attainment of a blood peak higher than that of the other formulations.

| Example 5 - Two layered tablet (fast and slow release) | |
|---|---|
| Fast release layer | |
| 1) Diclofenac potassium salt: | 15 mg |
| 2) Potassium bicarbonate: | 30 mg |
| 3) Lactose: | 13.2 mg |
| 4) Maize starch (intragranular): | 6 mg |
| 5) Methyl cellulose: | 0.12 mg |
| 6) Sodium laurylsulfate: | 0.06 mg |
| 7) Maize starch (extragranular): | 9 mg |
| 8) Crospovidone: | 0.6 mg |
| 9) Sodium carboxtmethylstarch: | 1.5 mg |
| 10) Magnesium stearate: | 2.7 mg |
| 11) Colloidal silicon dioxide: | 0.6 mg |
| Slow release layer | |
| 1) Diclofenac potassium salt: | 70 mg |
| 2) Potassium bicarbonate: | 30.8 mg |
| 3) Lactose: | 32.2 mg |
| 4) Polyvinylpyrrolidone: | 1.16 mg |
| 5) Hydrpxypropylmethylcellulose: | 70 mg |
| 6) Magnesium stearate: | 0.84 mg |
| 7) Colloidal silicon dioxide: | 0.21 mg |
| 8) Talc: | 3.92 mg |
| 9) Polyethylene glycol: | 0.56 mg |

| Example 6 - Drops | |
|---|---|
| 1) Diclofenac potassium salt: | 75 g |
| 2) Methyl p-oxybenzoate: | 2.7 g |
| 3) Propyl p-oxybenzoate: | 0.3 g |
| 4) Aspartame: | 37.5 g |
| 5) Potassium bicarbonate: | 37.5 g |
| 6) Glycerol: | 300 g |
| 7) Ethyl alcool: | 450 g |
| 8) Water q.s.: | 1500 g |
| Possible modifications: | |
| a) Addition of sodium metabisulfite (0.06%) | |
| b) Addition of sodium metabisulfite (0.06%) | |
| Mint flavouring (1.25%) | |
| Strawberry flavouring (0.75%) | |

| Example 7 - Drops | |
|---|---|
| 1) Diclofenac potassium salt: | 37.5 g |
| 2) Methyl p-oxybenzoate: | 2.7 g |
| 3) Propyl p-oxybenzoate: | 0.3 g |
| 4) Aspartame: | 37.5 g |
| 5) Potassium bicarbonate: | 18.75 g |
| 6) Saccharin: | 6.0 g |

-continued

| | |
|---|---|
| 7) Glycerol: | 300 g |
| 8) Ethyl alcool: | 450 g |
| 9) Water q.s.: | 1500 g |
| Possible modifications: | |
| a) Addition of sodium metabisulfite (0.03%) | |
| b) Addition of sodium metabisulfite (0.03%) | |
| Mint flavouring (1.25%) | |
| Strawberry flavouring (0.75%) | |

Example 8 - Mouthwash

| | |
|---|---|
| 1) Diclofenac potassium salt: | 0.75 g |
| 2) Glycerol: | 50 g |
| 3) Sorbitol: | 12 g |
| 4) Saccharin: | 0.5 g |
| 5) Aspartame: | 1.0 g |
| 6) Methyl p-oxybenzoate: | 0.5 g |
| 7) Propyl p-oxybenzoate: | 0.1 g |
| 8) Mint flavouring: | 1.0 g |
| 9) Ethyl alcool: | 100 g |
| 10) Potassium bicarbonate: | 0.33 g |
| 11) Water q.s.: | 500 ml |

Example 9 - Gum-paste

| | |
|---|---|
| 1) Diclofenac potassium salt: | 5.0 g |
| 2) Glycerol: | 630 g |
| 3) Sodium benzoate: | 5.0 g |
| 4) Silica (Wessalon S ® - Degussa): | 120 g |
| 5) Silica (Siddent 9 ® - Degussa): | 80 g |
| 6) Cellulose gum: | 3.0 g |
| 7) Polyethylenglycol 600: | 30 g |
| 8) Sodium lauroyl sarcosinate (or sodium lauryl sulfate): | 60 g |
| 9) Mint flavouring: | 10 g |
| 10) Sodium saccharin: | 1.0 g |
| 11) Aspartame: | 3.0 g |
| 12) Potassium bicarbonate: | 2.2 g |
| 13) Water q.s.: | 1 kg |

Example 10 - Tooth-paste

| | |
|---|---|
| 1) Diclofenac potassium salt: | 5.0 g |
| 2) Glycerol: | 630 g |
| 3) Sodium benzoate: | 5.0 g |
| 4) Silica (Wessalon S ® - Degussa): | 20 g |
| 5) Silica (Siddent 9 ® - Degussa): | 80 g |
| 6) Cellulose gum: | 3.0 g |
| 7) Polyethylenglycol 600: | 30 g |
| 8) Sodium lauroyl sarcosinate (or sodium lauryl sulfate): | 60 g |
| 9) Mint flavouring: | 10 g |
| 10) Sodium saccharin: | 1.0 g |
| 11) Aspartame: | 3.0 g |
| 12) NaF: | 1.0 g |
| 13) Na$_2$FPO$_3$: | 4.0 g |
| 14) Potassium bicarbonate: | 2.2 g |
| 15) Water q.s.: | 1 kg |

Example 11 - Tablet

| | |
|---|---|
| 1) Diclofenac potassium salt: | 50 mg |
| 2) Mannitol: | 50 mg |
| 3) Potassium bicarbonate: | 22 mg |
| 4) Maize starch (intragranular): | 10 mg |
| 5) Methyl cellulose: | 0.2 mg |
| 6) Sodium laurylsulfate: | 0.1 mg |
| 7) Maize starch (extragranular): | 15 mg |
| 8) Crospovidone: | 1.0 mg |
| 9) Sodium carboxymethylstarch: | 2.5 mg |
| 10) Magnesium stearate: | 4.5 mg |
| 11) Colloidal silicon dioxide: | 10 mg |

Example 12

Comparative Test

In the present experiment a sachet formulation containing 50 mg of Diclofenac potassium was compared to a bioequivalent sugar coated fast release tablet also containing 50 mg of Diclofenac potassium, produced and marketed in Italy by Novartis as Cataflam®.

The sachet formulation according to the present invention had the following composition:

| | |
|---|---|
| 1) Diclofenac potassium salt: | 50 mg |
| 2) Potassium bicarbonate: | 22 mg |
| 3) Mint flavour: | 50 mg |
| 4) Anice flavour: | 100 mg |
| 5) Saccharin sodium: | 4 mg |
| 6) Aspartame: | 10 mg |
| 7) Mannitol: | 50 mg |
| 8) Sucrose sugar crystals: | 1714 g |

The above test formulation and the Cataflam® formulation were administered as a single dose to 24 healty volunteers of both sexes. The pharmacokinetic parameters obtained with the two different formulations are reported in table 1 and in FIG. 5. As it will be easily appreciated, the rate of absorption was considerably faster with the sachet formulation of the present invention than with Cataflam®D, the sachet formulation having a higher average $C_{max}$ (2213 vs 1071 ng/ml) and a shorter average $T_{max}$ (0.228 vs 0.885 hours); furthermore, the $T_{max}$ of the sachet formulation shows a coefficient of variation lower than the reference formulation (16% vs 97%), this being an extremely important result from the clinical point of view regarding the healing of the pain in terms of quick time and repetability inter-subjects in order to reach the $C_{max}$.

Example 13

Comparative Test

Following to the excellent results obtained in example 12, two tablet formulations containing 12.5 or 25 mg of Diclofenac sodium salt and potassium bicarbonate (in the same weight ratio) have been prepared.

The tablet formulations had the following composition (in mg):

| Cores | | |
|---|---|---|
| Diclofenac sodium | 12.5 | 25 |
| Mannitol | 25 | 50 |
| Lactose monohydrate | 23.75 | 47.5 |
| Potassium bicarbonate | 5.5 | 11 |
| Maize starch | 22.5 | 45 |
| Methylcellulose | 0.075 | 0.15 |
| Sodium laurylsulphate | 0.125 | 0.25 |
| Crospovidone | 3 | 6 |
| Ultramyl | 5 | 10 |
| Coloidal silica | 0.55 | 1.1 |
| Cellulose microcrystalline | 0.5 | 1 |
| Magnesium stearate | 1.5 | 3 |
| Purified water q.s. | 100 | 200 |

-continued

| Coating | | |
|---|---|---|
| Opadry OY-35009 red | 2 | 4 |
| Macrogol 400 | 0.25 | 0.5 |

A four-way comparative bioavailability study was carried out on 18 healty volunteers of both sexes in order to evaluate the in vivo results of the pharmaokinetic profiles of the present formulations if compared to those of bioequivalent fast release formulations such as Cataflam® (25 mg of Diclofenac potassium) and Voltarol® (50 mg of Diclofenac sodium), both by Novartis. The results, which are summarized in FIG. 6, indicate that $T_{max}$ is prompter with the present formulations (T1=26 min, T2=24.6 min vs R1 71.4 min and R2= 40.8 min) and that $C_{max}$ is higher (T1=847 ng/ml and T2=861 ng/ml vs R1= 452 ng/ml and R2=703 ng/ml); furthermore, the $T_{max}$ of both present formulations shows a coefficient of variation lower than reference formulations (T1=46% and T2=49% vs R1=87% and R=96%).

Example 14

Comparative Test

A further comparative test was carried out on immediate release formulations according to the present invention, containing 50 mg of Diclofenac potassium and 22 mg of potassium bicarbonate, manufactured with different that is, respectively: T1=wet granulation using alcohol, T2=dry granulation by direct compression. The composition in mg of the two formulations is herebelow reported:

| | | |
|---|---|---|
| Diclofenac potassium | 50 | 50 |
| Potassium bicarbonate | 22 | 22 |
| Mannitol/pearlitol 400 DC | 119.9 | |
| Mannitol EP cf | | 50 |
| Maize starch | | 25 |
| Methocel A4C | | 0.2 |
| Sodium laurylsulphate | 0.1 | 0.1 |
| Polyplasdone XL | 6 | 1 |
| Ultramyl | | 2.5 |
| Magnesium stearate | 2 | 4.5 |
| Silicium aerosil | | 1 |
| Core mass | 200 | 156.3 |

A comparative bio availability study was carried out on 6 healty volunteers of both sexes in order to evaluate the in vivo results of the pharmaokinetic profiles of the present formulations if compared to those of a bioequivalent fast release formulation such Voltarene Rapid® (50 mg of Diclofenac potassium), both by Novartis. The results, which are reported in FIGS. 7–10 are also in this case excellent: the $T_{max}$ is in fact prompter with the present formulations (T1=18.6 min, T2=16.8 min vs R1=40.8 min) and the $C_{max}$ is higher (T1=1878.3 ng/ml and T2=1744.8 ng/ml vs R1=1307 ng/ml); furthermore, also in this case the $T_{max}$ of both present formulations shows a coefficient of variation lower than reference formulation (T1=12.9% and T2=25% vs R1=95.6%).

TABLE 1

Pharmacokinetic parameters for two different diclofenac formulations: test (Diclofenac potassium and reference (Diclofenac potassium salt sugar coated tablets)

| Vol. no. | $t_{max}$ (h) | | $C_{max}$ (ng/mL) | | $t_{1/2}$ (h) | | $AUC_{0-t}$ (ng · mL$^{-1}$ · h) | |
|---|---|---|---|---|---|---|---|---|
| | Test | Ref. | Test | Ref. | Test | Ref. | Test | Ref. |
| Vol. 1 | 0.250 | 0.500 | 1573.000 | 1186.211 | 1.505 | 0.939 | 1024.511 | 885.549 |
| Vol. 2 | 0.250 | 4.000 | 2382.368 | 965.100 | 0.875 | 1.358 | 1653.124 | 2092.036 |
| Vol. 3 | 0.184 | 1.000 | 2614.655 | 1352.400 | 0.796 | 1.610 | 1687.529 | 1763.484 |
| Vol. 4 | 0.250 | 3.000 | 2404.848 | 735.454 | 0.996 | 1.132 | 1881.944 | 1834.958 |
| Vol. 5 | 0.250 | 0.500 | 2971.457 | 1405.000 | 1.667 | 1.903 | 1819.756 | 1687.075 |
| Vol. 6 | 0.250 | 0.750 | 2158.700 | 1351.500 | 0.843 | 0.650 | 1197.716 | 1091.996 |
| Vol. 7 | 0.250 | 0.750 | 1739.200 | 1741.717 | 0.596 | 0.658 | 1448.713 | 1301.887 |
| Vol. 8 | 0.250 | 0.500 | 1715.350 | 534.300 | 0.818 | 1.111 | 991.864 | 1126.414 |
| Vol. 9 | 0.250 | 0.750 | 444.112 | 747.800 | 0.787 | 1.188 | 669.084 | 886.300 |
| Vol. 10 | 0.267 | 0.750 | 2350.100 | 1110.400 | 0.960 | 1.070 | 1327.808 | 1020.286 |
| Vol. 11 | 0.167 | 0.500 | 1867.200 | 1465.502 | 1.141 | 0.762 | 1337.821 | 892.870 |
| Vol. 12 | 0.167 | 0.500 | 4273.026 | 1432.200 | 1.052 | 0.697 | 1703.655 | 1139.003 |
| Vol. 13 | 0.250 | 0.500 | 2097.089 | 1155.371 | 1.313 | 1.198 | 1486.526 | 1233.531 |
| Vol. 14 | 0.167 | 0.250 | 2242.684 | 967.795 | 0.997 | 0.837 | 987.522 | 927.726 |
| Vol. 15 | 0.184 | 0.500 | 2040.247 | 1129.957 | 0.724 | 0.804 | 1213.725 | 1040.424 |
| Vol. 16 | 0.250 | 0.750 | 2143.692 | 818.200 | 0.560 | 1.199 | 1186.603 | 1250.221 |
| Vol. 17 | 0.250 | 1.500 | 1527.845 | 480.900 | 2.752 | 1.309 | 958.821 | 978.797 |
| Vol. 18 | 0.250 | 1.000 | 1859.608 | 666.500 | 1.630 | 1.383 | 1131.413 | 933.008 |
| Vol. 19 | 0.250 | 0.750 | 1537.508 | 770.100 | 1.726 | 1.137 | 980.348 | 906.275 |
| Vol. 20 | 0.250 | 0.250 | 1956.004 | 655.100 | 0.853 | 0.883 | 1309.289 | 1036.836 |
| Vol. 21 | 0.250 | 0.500 | 3551.360 | 2421.060 | 1.322 | 1.233 | 2147.217 | 1639.619 |
| Vol. 22 | 0.167 | 0.500 | 2464.978 | 1274.648 | 0.611 | 0.624 | 1038.817 | 816.924 |
| Vol. 23 | 0.167 | 0.750 | 2304.351 | 453.500 | 2.066 | 0.862 | 1161.414 | 1049.327 |
| Vol. 24 | 0.250 | 0.500 | 2901.504 | 894.337 | 0.970 | 1.279 | 1645.384 | 1086.512 |
| Mean | 0.228 | 0.885 | 2213.370 | 1071.461 | 1.148 | 1.076 | 1332.942 | 1192.544 |
| SD | 0.037 | 0.860 | 743.099 | 450.780 | 0.523 | 0.320 | 358.048 | 350.116 |
| CV % | 16.300 | 97.091 | 33.573 | 42.072 | 45.557 | 29.700 | 26.862 | 29.359 |
| Min. | 0.167 | 0.250 | 444.112 | 453.500 | 0.560 | 0.624 | 669.084 | 816.924 |
| Max. | 0.267 | 4.000 | 4273.026 | 2421.060 | 2.752 | 1.903 | 2147.217 | 2092.036 |

TABLE 1-continued

Pharmacokinetic parameters for two different diclofenac formulations: test (Diclofenac potassium and reference (Diclofenac potassium salt sugar coated tablets)

| | | | | | | | | |
|---|---|---|---|---|---|---|---|---|
| Geom. Mean | 0.225 | 0.692 | 2070.719 | 987.180 | 1.056 | 1.032 | 1287.195 | 1150.713 |
| Median | 0.250 | 0.625 | 2151.196 | 1039.098 | 0.983 | 1.122 | 1261.507 | 1067.920 |

| | $AUC_{0-\infty}$ (ng · mL$^{-1}$ · h) | | $C_1$ | | $C_{max}/AUC_{0-\infty}$ (h$^{-1}$) | | AUC extrapolated (%) | |
|---|---|---|---|---|---|---|---|---|
| Vol. no. | Test | Ref. | Test | Ref. | Test | Ref. | Test | Ref. |
| Vol. 1 | 1050.137 | 910.868 | 11.800 | 18.700 | 1.498 | 1.302 | 2.37 | 0.00 |
| Vol. 2 | 1693.172 | 2092.036 | 31.700 | 13.500 | 1.407 | 0.461 | 1.82 | 1.38 |
| Vol. 3 | 1718.755 | 1788.111 | 27.200 | 10.600 | 1.521 | 0.756 | 0.83 | 1.15 |
| Vol. 4 | 1897.754 | 1856.346 | 11.000 | 13.100 | 1.267 | 0.396 | 1.39 | 1.88 |
| Vol. 5 | 1845.486 | 1719.478 | 10.700 | 11.800 | 1.610 | 0.817 | 1.56 | 1.90 |
| Vol. 6 | 1216.693 | 1113.146 | 15.600 | 22.500 | 1.774 | 1.214 | 2.50 | 1.79 |
| Vol. 7 | 1485.867 | 1325.661 | 43.200 | 25.000 | 1.170 | 1.314 | 1.46 | 1.78 |
| Vol. 8 | 1006.522 | 1146.775 | 12.400 | 12.700 | 1.704 | 0.466 | 3.08 | 2.75 |
| Vol. 9 | 690.354 | 911.329 | 18.700 | 14.600 | 0.643 | 0.821 | 1.74 | 1.80 |
| Vol. 10 | 1351.357 | 1038.971 | 17.000 | 12.100 | 1.739 | 1.069 | 3.01 | 3.01 |
| Vol. 11 | 1379.311 | 920.579 | 25.200 | 25.200 | 1.354 | 1.592 | 1.62 | 2.03 |
| Vol. 12 | 1731.709 | 1162.638 | 18.500 | 23.500 | 2.468 | 1.232 | 1.26 | 1.56 |
| Vol. 13 | 1505.454 | 1253.088 | 10.000 | 11.300 | 1.393 | 0.922 | 2.58 | 2.26 |
| Vol. 14 | 1013.665 | 949.163 | 18.200 | 17.700 | 2.212 | 1.020 | 1.91 | 2.86 |
| Vol. 15 | 1237.399 | 1071.029 | 22.700 | 26.400 | 1.649 | 1.055 | 1.33 | 1.58 |
| Vol. 16 | 1202.653 | 1270.280 | 19.900 | 11.600 | 1.782 | 0.644 | 4.16 | 2.80 |
| Vol. 17 | 1000.433 | 1006.986 | 10.500 | 14.900 | 1.527 | 0.478 | 5.51 | 2.26 |
| Vol. 18 | 1197.411 | 954.597 | 28.100 | 10.800 | 1.553 | 0.698 | 2.57 | 2.11 |
| Vol. 19 | 1006.229 | 925.835 | 10.400 | 11.900 | 1.528 | 0.832 | 2.03 | 2.02 |
| Vol. 20 | 1336.472 | 1058.242 | 22.400 | 16.800 | 1.464 | 0.619 | 1.19 | 1.07 |
| Vol. 21 | 2173.030 | 1657.372 | 13.500 | 10.000 | 1.634 | 1.461 | 1.75 | 1.68 |
| Vol. 22 | 1057.293 | 830.908 | 21.000 | 15.500 | 2.331 | 1.534 | 3.13 | 1.80 |
| Vol. 23 | 1198.950 | 1068.588 | 12.600 | 15.500 | 1.922 | 0.424 | 2.19 | 1.94 |
| Vol. 24 | 1682.290 | 1108.024 | 26.400 | 11.700 | 1.725 | 0.807 | 2.10 | 1.78 |
| Mean | 1361.600 | 1214.169 | 19.113 | 15.725 | 1.620 | 0.914 | 2.213 | 1.883 |
| SD | 358.359 | 348.108 | 8.244 | 5.160 | 0.377 | 0.365 | 1.035 | 0.641 |
| CV % | 26.319 | 28.671 | 43.134 | 32.812 | 23.277 | 39.991 | 46.795 | 34.056 |
| Min. | 690.354 | 830.908 | 10.000 | 10.000 | 0.643 | 0.396 | 0.833 | 0.000 |
| Max. | 2173.030 | 2092.036 | 43.200 | 26.400 | 2.468 | 1.592 | 5.512 | 3.010 |
| Geom. Mean | 1316.580 | 1173.325 | 17.609 | 15.011 | 1.573 | 0.841 | 2.023 | // |
| Median | 1286.936 | 1089.527 | 18.350 | 14.050 | 1.582 | 0.827 | 1.974 | 1.843 |

What is claimed is:

1. A method for obtaining an average $T_{max}$ of diclofenac in a human patient between 5 and 30 minutes after administering said diclofenac to said patient, said average $T_{max}$ having a coefficient of variation (CV%) less than about 70%, comprising orally administering a diclofenac formulation to said patient, wherein said diclofenac formulation comprises diclofenac in acid and/or salt form together with an alkali metal bicarbonate selected from the group consisting of sodium bicarbonate, potassium bicarbonate and mixtures thereof, wherein said alkali metal bicarbonate is present in an amount of from about 20 to about 80% by weight based on the weight of said diclofenac, wherein said diclofenac formulation further contains a flavoring substance selected from the group consisting of mint, aniseed, ammonium glycyrrhizinate and mixtures thereof whereby palatability and astringency effects are eliminated, and wherein said diclofenac formulation is selected from:

a. a powder formulation dissolved or dispersed in water; and
   b. a fast release layer present in a two layered diclofenac tablet that comprises a slow release layer and a fast release layer.

2. The method according to of claim 1 where said average $T_{max}$ is reached 13–27 minutes after said administration.

3. A The method according to of claim 1 wherein said alkali metal bicarbonate is present in an amount of from about 40 to about 80% by weight based on the weight of said diclofenac.

4. The method of claim 1 wherein said diclofenac formulation comprises from about 10 to about 60 mg. of diclofenac in its potassium salt form.

5. The method of claim 1 wherein said diclofenac formulation comprises from about 10 to about 60 mg. of diclofenac in its sodium salt form.

6. The method of claim 1 wherein said alkali metal bicarbonate is sodium bicarbonate.

7. The method of claim 1 wherein said alkali metal bicarbonate is potassium bicarbonate.

8. The method of claim 1 wherein said diclofenac formulation is said powder formulation.

9. The method of claim 1 wherein said diclofenac formulation is said fast release layer.

10. The method of claim 1 wherein said diclofenac formulation is said powder formulation, and said diclofenac formulation comprises about 50 mg. of diclofenac potassium salt.

11. The method of claim 1 wherein said diclofenac formulation is said fast release layer, said diclofenac formulation comprises about 15 mg. of diclofenac potassium salt, and said slow release layer comprises about 70 mg. of diclofenac potassium salt.

12. The method of claim 1 wherein said diclofenac formulation comprises about 50 mg. of diclofenac potassium salt and from about 22 to about 24 mg. of potassium bicarbonate.

13. The method of claim 1 wherein said diclofenac formulation comprises about 50 mg. of diclofenac and said administration achieves an average $C_{max}$ of from about 1700 to about 2300 ng/ml.

14. A method of treating a human patient with diclofenac comprising orally administering a diclofenac formulation to said patient, wherein said diclofenac formulation comprises diclofenac in acid and/or salt form together with one or more alkali metal carbonates or bicarbonates, wherein said one or more alkali metal carbonates or bicarbonates is present in an amount of greater than about 20% by weight based on the weight of said diclofenac, and wherein said diclofenac formulation is selected from:
   a. a powder formulation dissolved or dispersed in water; and
   b. a fast release layer present in a two layered diclofenac tablet that comprises a slow release layer and a fast release layer.

15. The method of claim 14 wherein an average $T_{max}$ of diclofenac is reached between 5 and 30 minutes after orally administering said diclofenac formulation.

16. The method of claim 14 wherein an average $T_{max}$ of diclofenac is reached between 5 and 30 minutes after orally administering said diclofenac formulation, said average $T_{max}$ having a coefficient of variation (CV%) less than about 70%.

17. The method of claim 14 wherein said diclofenac formulation comprises about 50 mg. of diclofenac and said administering achieves an average $C_{max}$ of from about 1700 to about 2300 ng/ml.

18. The method of claim 14 wherein said diclofenac formulation comprises from about 10 to about 60 mg. of diclofenac in its potassium salt form.

19. The method of claim 14 wherein said diclofenac formulation comprises from about 10 to about 60 mg. of diclofenac in its sodium salt form.

20. The method of claim 14 wherein said one or more alkali metal carbonates or bicarbonates is present in an amount of from about 40 to about 80% by weight based on the weight of diclofenac.

21. The method of claim 14 wherein said diclofenac formulation comprises sodium bicarbonate.

22. The method of claim 14 wherein said diclofenac formulation comprises potassium bicarbonate.

23. The method of claim 14 wherein said diclofenac formulation is said powder formulation.

24. The method of claim 14 wherein said diclofenac formulation is said fast release layer.

25. The method of claim 14 wherein said diclofenac formulation is said powder formulation, and said diclofenac formulation comprises about 50 mg. of diclofenac potassium salt.

26. The method of claim 14 wherein said diclofenac formulation is said fast release layer, said diclofenac formulation comprises about 15 mg. of diclofenac potassium salt, and said slow release layer comprises about 70 mg. of diclofenac potassium salt.

27. The method of claim 14 wherein said diclofenac formulation comprises about 50 mg. of diclofenac potassium salt and from about 22 to about 24 mg. of potassium bicarbonate.

28. A method for obtaining an average $T_{max}$ of diclofenac in a human patient between 5 and 30 minutes after administration comprising orally administering a diclofenac formulation to said patient, wherein said diclofenac formulation comprises diclofenac in acid and/or salt form, and wherein said diclofenac formulation is selected from:
   a. a powder formulation dissolved or dispersed in water; and
   b. a fast release layer present in a two layered diclofenac tablet that comprises a slow release layer and a fast release layer.

29. The method of claim 28 wherein said average $T_{max}$ has a coefficient of variation (CV%) less than about 70%.

30. The method of claim 28 wherein said average $T_{max}$ is reached 13–27 minutes after administration.

31. The method of claim 28 wherein said diclofenac formulation comprises about 50 mg. of diclofenac and said administration achieves an average $C_{max}$ of from about 1700 to about 2300 ng/ml.

32. The method of claim 28 wherein said diclofenac formulation is said powder formulation.

33. The method of claim 28 wherein said diclofenac formulation is said fast release layer.

34. A method for obtaining an average $T_{max}$ of diclofenac in a human patient between 5 and 30 minutes after administration comprising orally administering a diclofenac formulation to said patient, wherein said diclofenac formulation comprises diclofenac in acid and/or salt form and means for enhancing said average $T_{max}$ of said diclofenac, and wherein said diclofenac formulation is selected from:
   a. a powder formulation dissolved or dispersed in water; and
   b. a fast release layer present in a two layered diclofenac tablet that comprises a slow release layer and a fast release layer.

35. The method of claim 34 wherein said average $T_{max}$ has a coefficient of variation (CV%) less than about 70%.

36. The method of claim 34 wherein said $T_{max}$ of diclofenac is reached 13–27 minutes after administration.

37. The method of claim 34 wherein said diclofenac formulation comprises about 50 mg. of diclofenac and said administration achieves an average $C_{max}$ of from about 1700 to about 2300 ng/ml.

38. The method of claim 34 wherein said means for enhancing said average $T_{max}$ of said diclofenac comprises one or more alkali metal carbonates or bicarbonates.

39. The method of claim 34 wherein said means for enhancing said average $T_{max}$ of said diclofenac comprises one or more alkali metal carbonates or bicarbonates in an amount of from about 20 to about 80% by weight based on the weight of said diclofenac.

40. The method of claim 34 wherein said means for enhancing said average $T_{max}$ of said diclofenac comprises sodium bicarbonate.

41. The method of claim 34 wherein said means for enhancing said average $T_{max}$ of said diclofenac comprises potassium bicarbonate.

42. The method of claim 34 wherein said diclofenac formulation is said powder formulation.

43. The method of claim 34 wherein said diclofenac formulation is said fast release layer.

* * * * *